United States Patent
Quirk

(10) Patent No.: US 7,238,371 B2
(45) Date of Patent: Jul. 3, 2007

(54) TRIGGERED RELEASE FROM PROTEINOID MICROSPHERES

(75) Inventor: Stephen Quirk, Alpharetta, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 465 days.

(21) Appl. No.: 10/840,557

(22) Filed: May 6, 2004

(65) Prior Publication Data
US 2004/0208937 A1    Oct. 21, 2004

Related U.S. Application Data

(62) Division of application No. 10/027,441, filed on Dec. 20, 2001, now Pat. No. 7,056,535.

(51) Int. Cl.
*A61K 9/16* (2006.01)
(52) U.S. Cl. .................. 424/499; 424/489; 424/491
(58) Field of Classification Search ................ None
See application file for complete search history.

(56) References Cited

U.S. PATENT DOCUMENTS

| | | | |
|---|---|---|---|
| 4,101,380 A | 7/1978 | Rubinstein et al. | |
| 4,925,673 A | 5/1990 | Steiner et al. | |
| 4,954,435 A | 9/1990 | Krauth | |
| 5,271,961 A | 12/1993 | Mathiowitz et al. | 427/213.31 |
| 5,399,331 A | 3/1995 | Loughery et al. | |
| 5,437,274 A | 8/1995 | Khoobehi et al. | 600/317 |
| 5,679,377 A | 10/1997 | Bernstein et al. | |
| 5,834,232 A | 11/1998 | Bishop et al. | |
| 6,180,140 B1 | 1/2001 | Leone-Bay et al. | 424/489 |
| 6,191,278 B1 | 2/2001 | Lee et al. | |
| 6,193,953 B1 | 2/2001 | Lohrmann et al. | |
| 6,232,295 B1 | 5/2001 | Kayyem et al. | |
| 6,413,550 B1 | 7/2002 | Milstein et al. | 424/499 |
| 6,541,606 B2 | 4/2003 | Margolin et al. | 530/350 |
| 6,576,263 B2* | 6/2003 | Truong et al. | 424/489 |
| 6,660,843 B1 | 12/2003 | Feige et al. | 530/391.7 |
| 6,902,892 B1 | 6/2005 | Salceda et al. | |
| 7,056,535 B2* | 6/2006 | Quirk | 424/499 |
| 2003/0118479 A1* | 6/2003 | Quirk et al. | 422/58 |
| 2003/0138975 A1* | 7/2003 | Quirk | 436/524 |

OTHER PUBLICATIONS

Faulstich, H., et al., 1993, "Derivitization of proteins with a new class of thiol-specific reagents", Chemistry of Peptides and Proteins, vol. 5, No. 6(PT. B), pp. 581-587.*

Faulstich, H., et al., 1993, "Interchain and intrachain crosslinking of actin thiols by a bihunctional thiol-specific reagent", FEBS Letters, vol. 302, No. 3, pp. 201-205.*

(Continued)

*Primary Examiner*—Nashaat T. Nashed
*Assistant Examiner*—William W. Moore
(74) *Attorney, Agent, or Firm*—Schwegman, Lundberg, Woessner, Kluth, P.A.

(57) ABSTRACT

The invention provides proteinoid microsphere made up of a mixture of thermally condensed amino acids that are crosslinked with a bis dithiol crosslinker reagent. The proteinoid microspheres of the invention may be used to encapsulate a material or a compound and to provide slow, sustained or timed release of the material or compound. The proteinoid microspheres are stable in solution until exposed to a reducing agent. However, the in vivo environment provides a sufficient reduction potential to provide slow, sustained release of materials contained therein from the proteinoid microspheres of the present invention.

15 Claims, 9 Drawing Sheets

OTHER PUBLICATIONS

Faulstich, H, et al., 1995, "Reversible introduction of thiol compounds into proteins by use of activated mixed disulfides", Methods in Enzymology, vol. 251(Biothiols, Part A), pp. 357-366.*

Kliche, W., et al., 1999, "Thiol-Specific Cross-Linkers of Variable Length Reveal a Similar Separation of SH1 and SH2 in Myosin Subfragment 1 in the Presence and Absence of MgADP", Biochemistry, vol. 38, No. 32, pp. 10307-10317.*

Green, N. S., et al., 2001, "Quantitative evaluation of the lengths of homobifunctional protein cross-linking reagents used as molecular rulers", Protein Science, vol. 10, No. 7, pp. 1293-1304.*

Junghans, M., "Phosphodiester And Phosphorothioate Oligonucleotide Condensation And Preparation of Antisense Nanoparticles", *Biochimica Et Biophysica Acta.*, 1544, (Jan. 2001), 177-188.

* cited by examiner

TRIGGERED RELEASE FROM PROTEINOID MICROSPHERES

This application is a divisional application of U.S. application Ser. No. 10/027,441 filed on Dec. 20, 2001 now U.S. Pat. No. 7,056,535 which is incorporated herein by reference.

FIELD OF THE INVENTION

The invention relates to proteinoid microspheres.

BACKGROUND OF THE INVENTION

Delivery of pharmaceutical and therapeutic agents is often severely limited by the chemical or physical barriers of the body. For example, oral administration of therapeutics is the route of choice. However, the extreme pH values and powerful digestive enzymes in the digestive system often destroy a therapeutic agent before it can get into the bloodstream and have any beneficial effect. Therapeutic agents such as biologically active peptides and proteins (e.g., insulin) are generally perceived to be unsuitable for oral administration because they are rapidly destroyed in the digestive system by acid hydrolysis and/or by proteolytic enzymes.

A great deal of research has been devoted to developing effective oral drug delivery methods and systems for these vulnerable therapeutic agents. For example, workers have attempted to co-administer the agent with an adjuvant such as a resorcinol containing a non-ionic surfactant like polyoxyethylene oleyl ether or n-hexadecyl polyethylene ether to increase the permeability of the intestinal walls. Other workers have attempted to co-administer therapeutic agents with enzyme inhibitors like pancreatic trypsin inhibitor, diisopropylfluorophosphate (DFF) and trasylol to avoid enzymatic degradation.

However, these approaches have limited applicability because the added reagents are toxic, interact negatively with the therapeutic agent, or fail to adequately protect the therapeutic agent or the uptake and absorption of the therapeutic agent.

Liposomes have also been used as drug delivery agents. They provide a layer of lipid around the encapsulated pharmacological agent. For example, the use of liposomes containing heparin is disclosed in U.S. Pat. No. 4,239,754. Several studies have been reported on the use of liposomes with insulin; e.g., Patel et al. (1976) FEBS Letters Vol. 62, page 60 and Hashimoto et al. (1979) Endocrinol. Japan, Vol. 26, page 337.

However, problems also exist for delivery with liposomes. Liposome suffer from poor stability, inadequate shelf life, small cargo loads (molecular weights generally less than 30,000), difficulty in manufacturing and adverse interactions with cargoes.

Artificial amino acid polymers or proteinoids that are form into microspheres have been described for encapsulating pharmaceuticals. See, e.g., Ma et al., 1994; Santiago et al., 1993; Madham Kumar and Pandurango Rao, 1998. Proteinoid microspheres can be formed by the thermal condensation of amino acids. The reaction joins carboxyl and amino groups that are part of an amino acid side chain or that are in the α position. A generalized scheme for a proteinoid thermal condensation reaction is illustrated below.

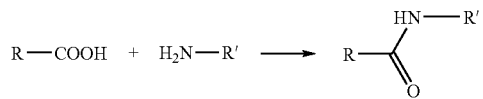

The carboxylate can be donated from either an amino acid sidechain (Asp or Glu) or from the α carboxylate. Similarly, the free amino group can be donated from either an amino acid sidechain (Arg, Lys, Asn, or Gln) or from the α amino group. It is relatively straightforward to produce proteinoids that are either acidic or basic via this simple thermal condensation reaction.

Such thermal condensation of simple amino acid mixtures was first described in the late 1950's by Harada and Fox (1958, 1960). This early work focused on linear polymers as model protein systems. It was not until 1964 that scientists realized that the thermal condensation of amino acids could result in the formation of spherical particles (Fox 1964). Proteinoid microspheres made in this manner can vary in size from 1 to 10 microns and some of them are hollow.

A proteinoid can be swelled in aqueous solution at moderate temperatures (usually around 50° C.) forming a structure known as a microsphere (see, e.g. Brooke and Fox, 1977). Several workers have formulated experimental models for 'communication' between proteinoid microspheres (Hsu et al., 1971 and Hsu and Fox, 1976) that involves conjugation and fusion of individual proteinoid microspheres. Considering the abiotic conditions on earth millions of years ago and the conditions leading to truly living complex assemblies, such workers have suggested that proteinoid microspheres could be involved in a natural transition from cell-like structures to actual cells.

Researchers have searched for enzymatic activity in proteinoid microsphere preparations. Most of the early work in this area was motivated by an interest in supporting an evolutionary role for proteinoid microspheres. Reports exist on the catalyzed formation of small linear peptides (Nakashima and Fox, 1980 and 1981; Fox and Nakashima, 1980), the activation of glycine (Ryan and Fox, 1973), and the formation of oligonucleotides (Jungck and Fox, 1973). Other reports describe proteinoid microsphere-mediated catalysis (Masinovsky, 1995), and the use of porphyrin complexed proteinoid microspheres as photosensitizers (Masinovsky et al., 1989). Yet a review of the literature reveals that proteinoid microspheres are actually devoid of what is generally defined as true enzymatic activity.

Once formed, thermal proteinoid microspheres are stable (Muller-Herold and Nickel, 1994; Syren, et al., 1985). In addition, thermal proteinoids are relatively easy to synthesize and characterize (Fox and Nakashima, 1966; Phillips and Melius, 1974; Luque-Romero et al., 1986; Kokufuta et al., 1983). A theoretical foundation for the assembly and self assembly of proteinoid microspheres has been formulated (Matsuno, 1981; Matsuno, 1981b). Some workers have even documented membrane-like electrical potential in proteinoid microspheres (Matsuno, 1984; Przybylski, 1985; Przbylski et al., 1982; Ishima, et al., 1981). Another report by Brooke and Fox (1977) describes the complex nature of proteinoid microsphere compartmentalization, including the responses of internal compartments to changes in temperature and pH.

U.S. Pat. No. 4,925,673 (the '673 patent) describes thermal proteinoid microspheres as well as methods for their preparation and use. However, the physicochemical properties of the proteinoid microspheres described in the '673 patent are not optimal. The light sensitivity, shelf life and the solubility in various portions of the gastrointestinal tract are limited. Additionally, there is a need for microspheres that can encapsulate a broader range of active agents such as lipophilic drugs.

Moreover, the method for making proteinoid microspheres described in the '673 patent provides a complex mixture of high molecular weight and low molecular weight peptide-like polymers which are difficult to separate. Only a small amount of the low molecular weight proteinoids form microspheres. Hence, an improved method of preparing of the proteinoids is also desired.

Accordingly, there is a need in the art for improved proteinoid microspheres as well as improved methods for their preparation.

SUMMARY OF THE INVENTION

The invention provides proteinoid microspheres having a molecular bridging agent that can be removed or opened upon exposure to a reducing agent. The invention also provides a method of forming a proteinoid microsphere that includes a molecular bridging agent that can be removed in a reducing environment. Removal of the bridge opens a hole or window in the proteinoid microspheres that allows the interior material to leak out. The rate at which the interior material traverses the proteinoid microspheres may be controlled by the size of the window, the number of windows and by the reduction potential in the environment. These proteinoid microspheres may be used to temporally treat a variety of complications including wounds (chronic or acute) by delivering a sequestered reagent in a controlled manner.

DETAILED DESCRIPTION OF THE INVENTION

Figure 1:
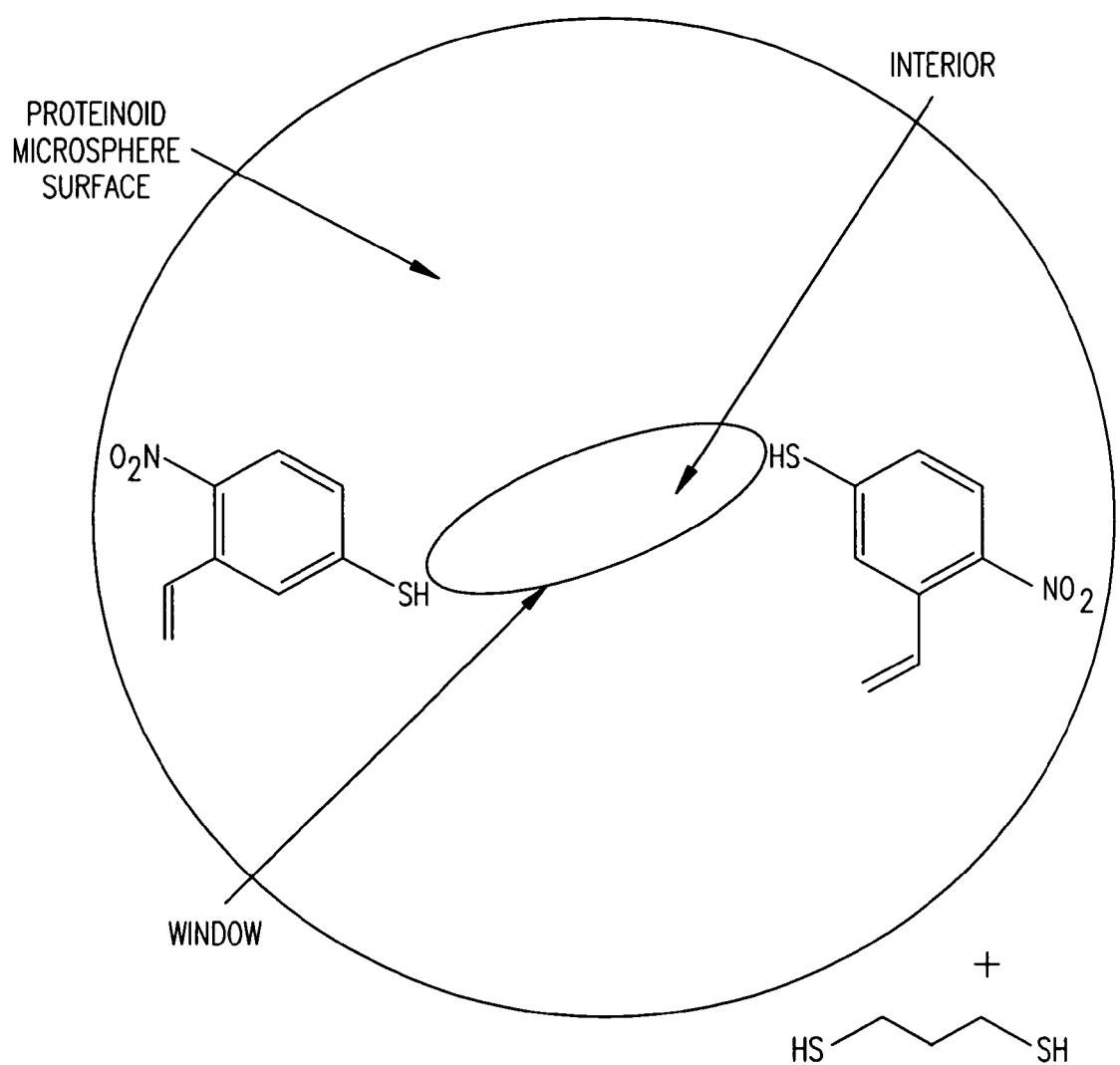
FIG. 1 provides a schematic representation of a windowed proteinoid microsphere. The surface of a proteinoid microsphere is depicted as a spherical particle with a C3 bis disulfide homobifunctional cross-linker. When the proteinoid microsphere is placed in a reducing environment, the disulfide bonds are reduced to free thiols and the C3 alkane bis thiol is released from the proteinoid microsphere. This creates a free space between the aryl thiols. This space, once occupied by the C3 alkane bis thiol, is open to the interior of the proteinoid microsphere. Hence any molecule trapped in the proteinoid microsphere interior can diffuse out from the proteinoid microsphere through this pore or window. The size of the alkane unit can be altered to control the diffusion rate or to properly accommodate larger or smaller encapsulated molecules.

The invention provides proteinoid microspheres comprising bifunctional cross-linking agents that can be partially removed by introduction of a reducing agent. These proteinoid microspheres may be used as delivery agents for pharmaceuticals and therapeutic agents. After formation, the proteinoid microspheres are stable and the pharmaceutical or therapeutic agent does not leak out until the proteinoid microspheres are exposed to a reducing environment. The rate of release of the pharmaceutical or therapeutic agent from the proteinoid microsphere may be modified, for example, by the choice of the type and percentage of cross-linking agent used to form the proteinoid microspheres.

Cross-linkers useful in the invention include bifunctional sulfhydryls having two dithio groups linked by a spacer region. Such crosslinking compounds can have any of the structures provided by formulae I–IV.

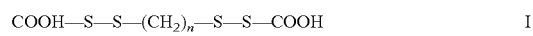
$$COOH-S-S-(CH_2)_n-S-S-COOH \qquad\qquad I$$

$$COOH-S-S-X-S-S-COOH \qquad\qquad II$$

$$NH_2-S-S-(CH_2)_n-S-S-NH_2 \qquad\qquad III$$

$$NH_2-S-S-X-S-S-NH_2 \qquad\qquad IV$$

Aryl—S—S—(CH$_2$)$_n$—S—S—Aryl      V

Aryl—S—S—X—S—S-Aryl      VI wherein:

X is a spacer group of about approximately 3 to 100 angstroms by about 2 to 30 angstroms that comprises an alkane chain, an alkene chain, a cyclealkyl or aryl ring having five to fourteen carbon atoms, or a combination thereof;

n is an integer ranging from 1 to 18;

S is a sulfur atom; and

Aryl denotes a phenyl radical or an ortho-fused bicyclic radical having about nine to ten ring atoms in which at least one ring is aromatic. Each Aryl moiety is substituted with at least one reactive group capable of forming a covalent linkage with an amino acid. Reactive groups capable of forming a covalent linkage with an amino acid include carboxylate, nitro, amino, sulfhydryl, and similar groups. A desirable reactive group is a carboxylate group.

One desirable crosslinking reagent is provided by formula VII.

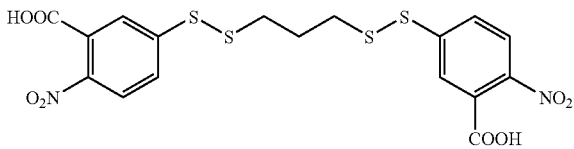

While an alkane chain containing three carbon atoms (C3) is depicted in formula II, desirable crosslinking reagents can have one (C1) to fifteen (C15) carbon atoms in the spacer between the two aryl disulfides. More desirable crosslinking reagents have two (C2) to twelve (C12) carbon atoms in the spacer between the two aryl disulfides. Even more desirable crosslinking reagents have two (C3) to nine (C9) carbon atoms in the spacer between the two aryl disulfides.

Proteinoid microspheres with different release rates can be prepared by varying the length of the spacer between the two aryl disulfide moieties of the crosslinking reagent. In general, a faster release rate is obtained by using a crosslinking reagent with a longer spacer.

The crosslinking reagent is incorporated into the forming proteinoid via condensation between the reactive groups of the crosslinking reagent and the free amino or carboxylate groups of the amino acids. In one embodiment, the reactive group is carboxylate that condenses with free amino groups of the amino acids used to form the proteinoid microsphere. In another embodiment, a reactive group is chosen that does not react with the amino or carboxylate groups of the amino acids. Instead, the reactive group is chosen to react with a selected amino acid side chain. The amount of cross-linking can then be controlled by varying the amount of the selected amino acid side chain.

The amount of crosslinking reagent used can vary. One of skill in the art can control the number of pores or windows formed in a proteinoid microsphere by altering the ratio of cross-linker to total amino acid. For example, the crosslinking reagent can form about 0.01% to about 20% of the proteinoid microsphere composition. Desirable proteinoid microsphere compositions contain about 0.1% to about 15% crosslinking reagent. More desirable proteinoid microsphere compositions contain about 1% to about 10% crosslinking reagent.

Some branching between crosslinked and thermally condensed amino acids is desirable to facilitate formation of spherical proteinoids. Hence, the type and amount of crosslinking reagent selected should permit branching. Care should be taken to ensure that excessive crosslinker is not used so that branching is eliminated or excessively inhibited. The type of amino acid utilized in the proteinoid microspheres can also influence the amount of branching. For example, when the reactive group on the crosslinking reagent reacts with carboxylate and/or amino groups, amino acids with carboxylate and/or amino group side chains can be used to encourage branching.

Proteinoids are synthesized by any method available to the skilled artisan. For example, proteinoids can be synthesized by procedures outlined in Fox and Nakashima, 1966; Phillips and Melius, 1974; Luque-Romero et al., 1986 with the modification that the crosslinking reagent is added. The incorporation of the cross-linking agent has no deleterious effects on the formation of either the proteinoid material or on the subsequent formation of proteinoid microspheres.

Specifically, dry amino acids and cross-linker can be mixed together, for example, by grinding in a mortar and pestle until completely mixed. Mixing time can vary as needed. Approximate times for mixing are five minutes to one hour. In one embodiment, mixing is done for about thirty minutes. The resulting powder can be further mixed via sonication, for example, using a water sonicating bath. Sonication can be done for about ten minutes to about four hours. In one embodiment, sonication was for about two hours.

The amino acid-crosslinker powder mixture is heated at a first temperature for several hours. The first temperature can vary, for example from about 150° C. to about 220° C. In one embodiment, the first temperature was about 190° C. Heating times at this first temperature can also vary somewhat, for example, from six to twelve hours. In one embodiment, the mixture was heated at about 190° C. for about nine hours. After heating at the first temperature, the temperature was raised to a second, higher temperature for several more hours. The second temperature can vary, for example, from temperature about 200° C. to about 220° C. In one embodiment, the second temperature was about 220° C. The time for heating at this second temperature can vary, for example, from about one hour to about six hours. In one embodiment, the mixture was heated at a second temperature of about 220° C. for about three hours. It is desirable to maintain a blanket of dry nitrogen gas over the amino acid mixture at all times. Over the course of the reaction, the amino acid— crosslinker mixture can change from an off white powder to a yellowish-brown semi-solid.

After heating, the reaction mixture is cooled to room temperature, and the solid material is resuspended in an excess of water. This process can be aided by sonication and stirring. Insoluble matter can be removed from the mixture by centrifugation, for example, at 3,000×g for 10 minutes at 25° C. The supernatant from such a centrifugation is collected. The proteinoid materials can be further purified by dialysis against water using, for example, a 3500 MWCO dialysis membrane. The proteinoid materials can be dried for easy storage, for example by lyophilization.

This process incorporates the cross-linker into the proteinoid microspheres with the two disulfides groups intact.

When the proteinoid microsphere is fully formed a small molecule can be loaded into the proteinoid microsphere interior. This is done by resuspended the proteinoid material into a convenient aqueous solution, for example, a buffer or a buffered saline solution. The pharmaceutical or therapeutic agent is added to the suspension at a concentration that will yield a protenoid microsphere preparation that contains a therapeutically effective amount of the pharmaceutical or therapeutic agent in a convenient dosage. The suspension is then heated for a time and to a temperature sufficient for the pharmaceutical or therapeutic agent to enter the protenoid microspheres. For example, in one embodiment, the proteinoid microspheres were heated to about 50° C. for about 15 minutes. The suspension is allowed to slowly cool to an temperature convenient for handling, for example, room temperature. During the cooling process microspheres form and precipitate from solution. The microspheres can be dialyzed versus or filtered to remove unencapsulated materials. If desired, the microspheres can be dried prior to use.

Such a loaded protenoid microsphere complex is stable until it is exposed to a reducing agent.

A schematic representation of a loaded proteinoid microsphere is depicted in FIG. 1. The surface of the proteinoid microsphere is a mixture of amino acids linked with a cross-linking reagent that has a three carbon (C3) spacer. When the proteinoid microsphere is placed in a reducing environment, the disulfide bonds in the crosslinking reagent are reduced to free thiols and the C3 alkane disulfide spacer is released from the proteinoid microsphere. This creates a free space between the aryl thiols. This space, once occupied by the C3 alkane disulfide, is open to the interior of the proteinoid microsphere. Hence, any molecule trapped in the proteinoid microsphere interior can diffuse out from the proteinoid microsphere through this window. The size of the alkane unit can be altered to control the diffusion rate or to properly accommodate larger or smaller interior diffusible molecules.

Molecular modeling indicates that the size of the pore created by loss of the C3 alkane disulfide spacer moiety is approximately 6 to 12 angstroms by about 3 angstroms. One of skill in the art can vary the size of pore opening by varying the size of the spacer within the crosslinking agent number of carbons. The exact window dimension will also depend on the proteinoid microsphere local structure.

Moreover, one of skill in the art can control the number of pores in a proteinoid microsphere by altering the crosslinker to total amino acid ratio as well as by modulating the type of reactive group on the crosslinking agent so that it will react with only a limited number of groups on the amino acids.

Accordingly, the rate of diffusion or release of the material encapsulated by the proteinoid microspheres of the invention is dependent upon three factors. The first factor is the size and concentration of the compounds in the proteinoid interior. The second factor is the size of the hole in the proteinoid microsphere, which is governed by the number of carbon atoms in the spacer group of the crosslinking reagent. The third factor that governs the release rate is the reduction potential of the environment. All three variables can be modulated to produce desired release kinetics.

In certain circumstances it may be difficult to modulate the reduction potential of the environment. In these situations, the size and amount of crosslinking agent as well as the size and concentration of the therapeutic agent can be varied to fine tune the release kinetics.

Reducing agents that can be used in the invention include any reagent that can reduce a disulfide bond. For example, reducing agents contemplate include dithiothreitol (DTT), and related compounds.

Amino Acids

Amino acids that can be used in the proteinoid microspheres of the invention can be genetically encoded L-amino acids, naturally occurring non-genetically encoded L-amino acids, synthetic L-amino acids or D-enantiomers of any of the above. The amino acid notations used herein for the twenty genetically encoded L-amino acids and common non-encoded amino acids are conventional and are as shown in Table 1.

TABLE 1

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| β-Alanine | | bAla |
| 2,3-Diaminopropionic acid | | Dpr |
| α-Aminoisobutyric acid | | Aib |
| N-Methylglycine (sarcosine) | | MeGly |
| Ornithine | | Orn |
| Citrulline | | Cit |
| t-Butylalanine | | t-BuA |
| t-Butylglycine | | t-BuG |
| N-methylisoleucine | | MeIle |
| Phenylglycine | | Phg |
| Cyclohexylalanine | | Cha |
| Norleucine | | Nle |
| Naphthylalanine | | Nal |
| Pyridylalanine | | |
| 3-Benzothienyl alanine | | |
| 4-Chlorophenylalanine | | Phe(4-Cl) |
| 2-Fluorophenylalanine | | Phe(2-F) |
| 3-Fluorophenylalanine | | Phe(3-F) |
| 4-Fluorophenylalanine | | Phe(4-F) |
| Penicillamine | | Pen |
| 1,2,3,4-Tetrahydroisoquinoline-3-carboxylic acid | | Tic |
| β-2-thienylalanine | | Thi |
| Methionine sulfoxide | | MSO |
| Homoarginine | | hArg |
| N-acetyl lysine | | AcLys |
| 2,4-Diamino butyric acid | | Dbu |
| ρ-Aminophenylalanine | | Phe(pNH$_2$) |
| N-methylvaline | | MeVal |
| Homocysteine | | hCys |
| Homoserine | | hSer |
| ε-Amino hexanoic acid | | Aha |
| δ-Amino valeric acid | | Ava |
| 2,3-Diaminobutyric acid | | Dab |

Surprisingly, amino acid composition plays a minimal role in altering release rates of the proteinoid microspheres. Any of the above amino acids, including both D and L enantiomers of these amino acids can be incorporated into the proteinoid microspheres. Mixtures can be as complex or as simple as desired. Increased functionality can be built into a proteinoid microsphere by including such amino acids as tyrosine (to utilize the hydroxyl group), cysteine (to utilize the thiol), phenylalanine (or other hydrophobic amino acids to alter solubility and proteinoid microsphere binding character), or tryptophan (to be used as an intrinsic fluorescence probe).

In addition, amino acids can be selected for incorporation into a proteinoid microsphere that are themselves therapeutically significant, such as arginine for chronic wounds. Since the proteinoid microsphere will ultimately be proteolyzed, the liberated amino acids themselves can provide an added nutritional benefit.

Therefore, a useful property of the present proteinoid microspheres is that there is a wide degree of latitude to their construction and composition. This latitude means that proteinoid microspheres can be individually tailored to perform any function in any environment.

Encapsulated Agents

The protenoid microspheres provided by the invention represent a new form of delivery vehicle for a broad range of applications, including therapeutic, pharmaceutical, agricultural and related applications. For example, the proteinoid microspheres can be used to encapsulate any material chosen by one of skill in the art for slow, sustained or timed release. The proteinoid microspheres can be used in any environment selected by one of skill in the art, for example, for therapy, for wound treatment, and for agricultural formulations. Materials encapsulated and released from the proteinoid microspheres of the invention include, for example, a thereapeutic agent, a pharmaceutical, an antiseptic reagent, a chemical compound, a peptide, a protein, an antibody, an oligonucleotide, a nucleic acid, a lipid, a carbohydrate, a fertilizer, a herbicide, an insecticide, or any other molecule chosen by one of skill in the art. In one embodiment the proteinoid microspheres are used for chronic wound treatment, where the molecule in the proteinoid microsphere interior is a healing agent.

The only determinant in the choice of the material encapsulated by the proteinoid microspheres of the invention is the ability of the compounds within the material to diffuse through the hole in the proteinoid microsphere. Greene et al. (2001) have measured the distances between the thiol groups in this class of spacer compound, observing a distance of about 6.9 angstroms for a C3 spacer and about 12.2 angstroms for a C9 spacer. If one assumes that the resulting pore is roughly rectangular, then the width of the pore would be approximately 3 angstroms. Heterogeneity in pore dimensions likely exists within a proteinoid microsphere and between proteinoid microspheres due to random thermal condensation between amino acids and crosslinking reagents (see, e.g., Madhan Kumar et al., 1998). However, the minimum square area of pores opened in the proteinoid microspheres illustrated in the Examples of this application are between 20 and 37 square angstroms. Of course it is possible to synthesize larger spacer molecules for other applications. This means a wide array of materials and molecules can be released used with the proteinoid microsphere system of the invention.

Compositions

The proteinoid microspheres of the invention can be formulated to contain a therapeutic agent and prepared as a pharmaceutical composition that can be administered to a mammalian host, such as a human patient. Such compositions can be adapted to the chosen route of administration. Administration can be oral, parenteral, intravenous, intramuscular, topical, transdermal or subcutaneous.

Therapeutic agents can be encapsulated by the present proteinoid microspheres by warming a suspension of proteinoids in a solution containing the therapeutic agent for a time and at a temperatue sufficient for the therapeutic agent to be encapsulated by the proteinoid microspheres. One of skill in the art can readily determine the optimal temperature for encapsulation, for example, by warming the suspension of proteinoids in a solution of the therapeutic agent, then collecting the proteinoid microspheres and observing whether the therapeutic agent has been encapsulated within the proteinoid microsphere. Thus, the temperature chosen for encapsulation can vary. Desired temperatures are about 30° C. to about 70° C. More desirable temperatures are about 40° C. to about 60° C. In one embodiment the proteinoid microspheres were heated at about 50° C. for about 15 minutes in a solution of the agent to be encapsulated. After heating, the suspension of proteinoid microspheres and therapeutic agent is allowed to slowly cool to room temperature. During such cooling the microspheres encapsulate the therapeutic agent and precipitate from solution. Once formed, the encapsulating proteinoid microspheres are stable in a non-reducing environment and can be washed, filtered, dialysed, and dried prior to use.

The compositions of the invention that include a therapeutic agent encapsulated by a proteinoid microsphere can be administered in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and so forth. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and so forth. The proteinoid microsphere composition may be suspended in a syrup or elixir that can contain sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed.

The proteinoid microsphere compositions may also be administered intravenously or intraperitoneally by infusion or injection. Suspensions of the proteinoid microspheres can be prepared in water or saline and optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the therapeutic agent encapsulated by the proteinoid microspheres and adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride.

Sterile injectable solutions may be prepared by incorporating the active compound in the required amount in the appropriate solvent with various of the other ingredients enumerated above, as required, followed by filter sterilization. In the case of sterile powders for the preparation of sterile injectable solutions, preferred methods of preparation include vacuum drying and the freeze drying techniques, which yield a powder of the proteinoid microspheres with the active ingredient plus any additional desired ingredient present in the previously sterile-filtered solutions.

For topical administration, the proteinoid microspheres may be applied directly to the skin or the wound or suspended in liquid and then applied. The proteinoid microspheres can also be administered to the skin as compositions or formulations, in combination with a dermatologically acceptable carrier, which may be a solid or a liquid.

Useful solid carriers include wound dressings, bandages, and the like that can have an absorbent material into which the proteinoid microsphere compositions of the invention are impregnated. Useful liquid carriers include water, alcohols or glycols or water-alcohol/glycol blends, in which the present proteinoid microspheres are dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and so forth, for application directly to the skin of the user.

Examples of useful dermatological compositions that can be used to deliver the compounds of formula I to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the therapeutic agents within the proteinoid microspheres of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of encapsulated proteinoid microspheres in the compositions is from about 0.1% to about 95% by weight. More desired concentrations of encapsulated proteinoid microspheres are from about 10.0% to about 85% by weight Even more desired concentrations of encapsulated proteinoid microspheres are from about 25% to about 75% by weight. The concentration in a semi-solid or solid composition such as a gel or a powder will be about 10% by weight to about 99% by weight, preferably about 50% by weight to about 95% by weight.

The amount of therapeutic agent required for use in treatment will vary not only with the particular salt selected but also with the route of administration, the nature of the condition being treated and the age and condition of the patient and will be ultimately at the discretion of the attendant physician or clinician.

The proteinoid microspheres are conveniently administered in unit dosage form; for example, containing 5 μg to about 100 mg, conveniently about 10 μg to about 50 mg, most conveniently, about 100 μg to about 10 mg per unit dosage form.

Ideally, the therapeutic agent is administered to achieve sustained peak plasma concentrations of from about 0.1 to about 10 nM, desirably, about 0.2 to 10 nM, most desirably, about 0.5 to about 5 nM. This may be achieved, for example, by the intravenous injection of a 0.05 to 5% suspension of the proteinoid microspheres, optionally in saline, or orally administered as a bolus containing about 1–100 mg of the proteinoid microspheres. Desirable blood levels are maintained by the sustained low level release of the therapeutic agent from the proteinoid microspheres. Intermittent infusion or administration of the encapsulated therapeutic agent can be performed as needed, for example, once or twice daily when the plasma level of the therapeutic agent declines to suboptimal levels.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations such as multiple topical applications in order to optimize treatment of a wound or skin condition. For example, it is desirable to administer the proteinoid microspheres topically to chronic wounds over an extended period of time to reverse the cyclic of tissue destruction within the wound.

The invention will be further described by reference to the following detailed examples, which are given for illustration of the invention, and are not intended to be limiting thereof.

EXAMPLE 1

Materials and Methods

Materials

L-amino acids and dithiothretiol, and any buffer reagents were obtained from Sigma Chemical Co. (St. Louis, Mo.), aryl disulfide homo bifunctional cross-linkers were purchased from Pierce, and the Pacific Blue fluorophore was acquired from Molecular Probes, Inc.

Proteinoid Formation

Synthesis of proteinoids generally followed the procedures outlined in the scientific literature (e.g.—Fox and Nakashima, 1966; Phillips and Melius, 1974; Luque-Romero et al., 1986). Specifically, dry amino acids and cross-linker were mixed together and ground in a mortar and pestle until completely mixed (approximate time 30 minutes). The resulting powder was further mixed via sonication in a water sonicating bath for two hours. The final powder was transferred into a glass vessel and was immersed into a mineral oil bath.

Three different proteinoids were prepared. The first preparation of proteinoid microspheres (PM1) contained 0.25 g of glutamic acid, 0.25 g of aspartic acid, 0.1 g of lysine, 0.1 g of leucine, 0.1 g alanine, 0.1 g arginine, and 0.1 g of C6 aryl disulfide reagent. The second preparation of proteinoid microspheres (PM2) contained the same composition as PM1, except that a C3 aryl disulfide reagent was employed and histidine was substituted for alanine. The third composition of proteinoid microspheres (PM3) contained 1.3 g of aspartic acid, 2.9 g of glutamic acid, 5.0 g of lysine, 2.5 g of leucine, 2.3 g of proline, and 0.5 g of C6 aryl disulfide reagent.

The mixtures were heated in the mineral oil bath at a temperature of 190° C. for nine hours. After nine hours, the temperature was raised to 220° C. for three hours. A blanket of dry nitrogen gas was maintained over the amino acid mixture at all times. Over the course of the reaction, the mixture changed from an off white powder to a yellowish-brown semi-solid. The reaction was cooled to room temperature, and the solid material was resuspended in an excess of water (usually about 10 mLs). This process was aided by sonication and stirring. The mixture was centrifuged at 3,000×g for 10 minutes at 25° C. in order to remove insoluble matter. The decanted solution was dialyzed extensively against water (1 L with multiple changes over a 48 hour period at 25° C.) using a 3500 MWCO dialysis membrane. The contents of the dialysis bag were returned to dryness via lyophilization.

Microsphere Formation

Dried proteinoids (200 mg) were resuspended in 20 mL of 10 mM Tris (pH 7.1). To this solution was added 10 mg of Pacific Blue fluorophore (final concentration 2 mM). The solution was heated to 50° C. for 15 minutes in a beaker containing 100 mL of water. The beaker was removed from the hot plate and was allowed to come to room temperature over an approximate one hour period. During the cooling process microspheres formed and precipitated from solution. The mixture was either dialyzed versus 1 L of 10 mM Tris (pH 7.1) overnight at room temperature or was filtered through Whatman filter paper, washed with 10 mM Tris (pH 7.1), and collected. The microspheres were dried prior to use.

Fluorescence Assays

All fluorescence experiments were conducted using a Shimadzu RF5301 fluorometer. Samples were slowly stirred to avoid proteinoid microsphere settling for both kinetic and steady state measurements.

The fluorophore used was Pacific Blue from Molecular Probes, Inc. The structure of Pacific Blue is provided below.

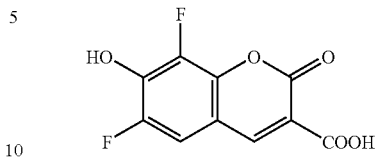

The excitation and emission wavelengths used for the Pacific Blue fluorophore were 405 nm and 450 nm respectively. Both excitation and emission monochrometer slits were set at 1.5 nm.

Proteinoid microsphere preparations were diluted into 10 mM Tris-HCl (pH 7.1) to a final concentration of 10% (v/v). They were added to the sample cuvette and slowly stirred. The intrinsic fluorescence of the sample was measured and was subtracted from subsequent scans. Dithiothreitol (DTT), at various concentrations, was then added to the sample cuvette. Scans were immediately initiated. For fluorescence emission intensity scans, the scan rate was set to medium, and an emission wavelength range of 300 to 600 nm was scanned. Emission intensity curves were corrected for scattering at 405 nm.

All steady state fluorescence intensity measurements were corrected for dilution (where appropriate) and inner filter effects according to the relation (Lakowicz, 1983):

$$F_{corr} = (F - B)\left(\frac{V}{V_o}\right)10^{0.5b(A\lambda_{ex})}$$

where $F_{cor}$ is the corrected fluorescence intensity, F is the measured fluorescence intensity, B is the background, V is the volume of the sample, $V_o$ is the initial sample volume, b is the cuvette pathlength, and $A\lambda_{ex}$ is the absorbance of the sample at 295 nm.

Self-quenching by relatively high local concentrations of the fluorophore inside the proteinoid microsphere provides a basis for measuring the release of a fluorescent entity from the proteinoid microspheres. Once diffusion begins, the fluorophore is significantly diluted in the cuvette, is no longer self quenched, and fluorescence emission can be detected. Other assays have been used and are described in the liposome literature.

EXAMPLE 2

Proteinoid Microsphere Properties

The PM1 preparation, made as described in Example 1, is completely stable in a non-reducing buffer system. When no reducing agent is present, there is no increase in fluorescence emission intensity at 450 nm (or any change in intensity as a function of time at any wavelength). Upon the addition of the reducing agent DTT there is a rapid increase in the fluorescence emission intensity at 450 nm. These results are shown in FIG. 2 and in FIG. 3 for PM3.

Figure 2:
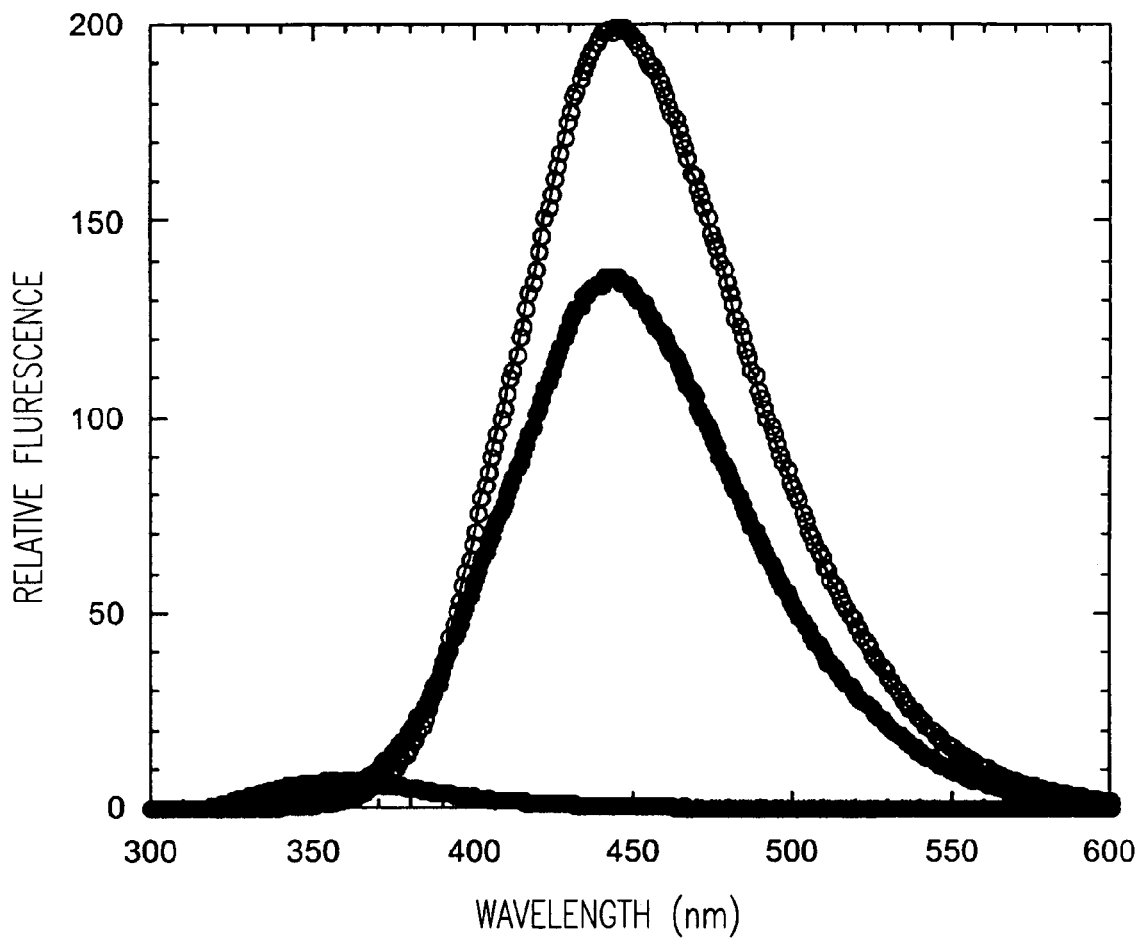
FIG. 2 provides fluorescence emission intensity spectra for the PM1 proteinoid microsphere preparation reacted with 0.01 mM DTT. The spectra were taken at time points prior to the addition of DTT, at one minute, and four minutes post the addition of DTT (curves from lowest to highest value at 450 nm respectively). As can be seen by the fluorescence emission intensity curves, the PM1 loaded with Pacific Blue fluorophore self quenches due to the relatively high concentration of Pacific Blue in the interior. As fluorophore exits PM1, the fluorescence intensity increases due to the instantaneous dilution of the fluorophore into the cuvette volume.

FIG. 2 provides fluorescence emission intensity spectra for PM1 reacted with 0.01 mM DTT. The fluorescence emission was observed at time points prior to the addition of DTT, at one minute, and four minutes post the addition of DTT (curves from lowest to highest value at 450 nm respectively). As can be seen by the fluorescence emission intensity curves, PM1 loaded with fluorophore self quenches due to the relatively high concentration of Pacific Blue in the interior. However, as fluorophore exits PM1 when a reducing agent is added, the fluorescence intensity increases due to the instantaneous dilution of the fluorophore into the cuvette volume.

Figure 3:
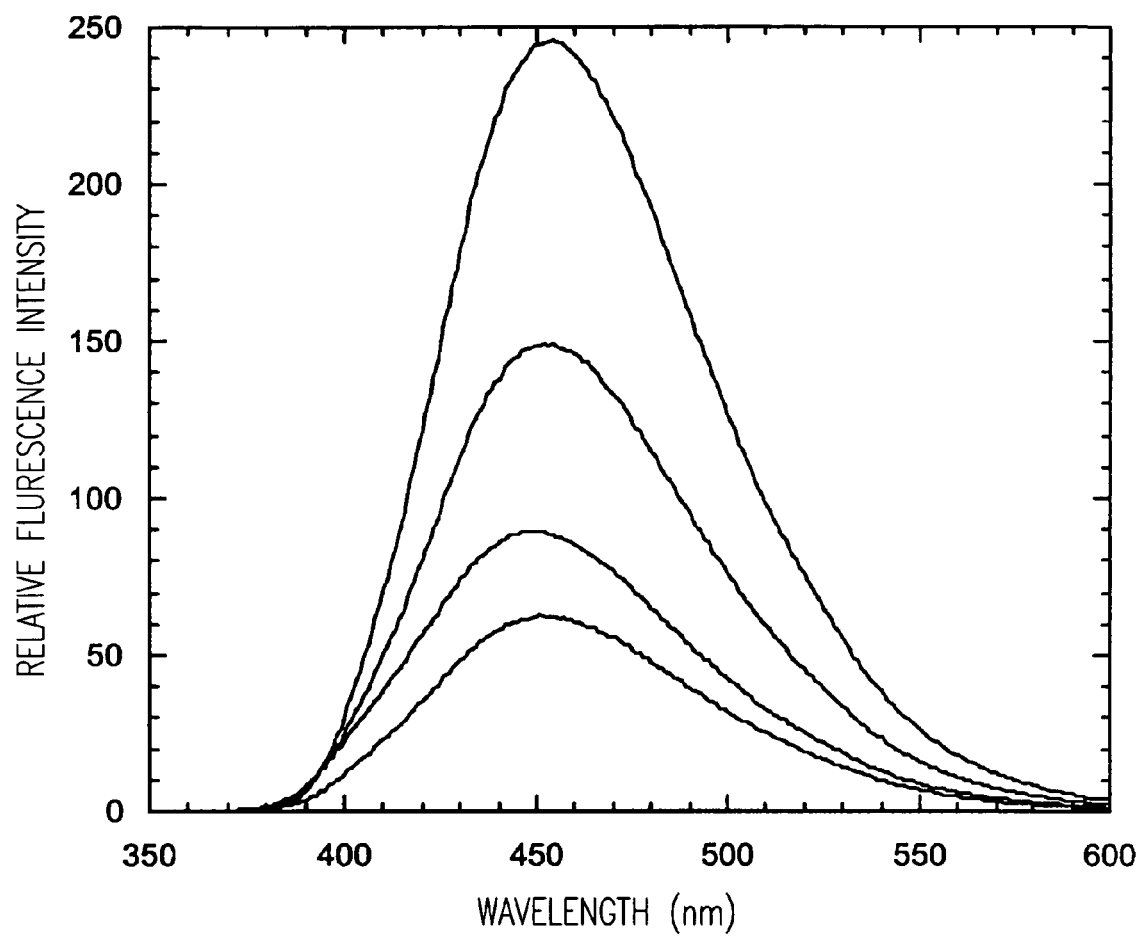
FIG. 3 provides a fluorescence emission intensity spectrum for PM3 reacted with 0.01 mM DTT. The spectra curves are time points taken immediately after addition of DTT (approximate elapsed time 10 seconds), at 30 seconds, one minute, and four minutes post the addition of DTT (curves from lowest to highest value at 450 nm respectively).

FIG. 3 provides fluorescence emission intensity spectra for PM3 reacted with 0.01 mM DTT. The spectra were taken immediately after addition of DTT (approximate elapsed time 10 seconds), at 30 seconds, at one minute, and at four minutes post-addition of DTT (curves from lowest to highest value at 450 nm respectively).

The emission intensity spectra are broad, showing positive features above background between 375 and 575 nm. This broadening is greater than observed for the fluorescence emission spectrum of free Pacific Blue in a similar buffer system and may indicate some secondary interactions with the proteinoid microsphere. The emission intensity maximum is not broad however, indicating that the fluorophore remains intact during microsphere formation and subsequent processing.

Figure 4:
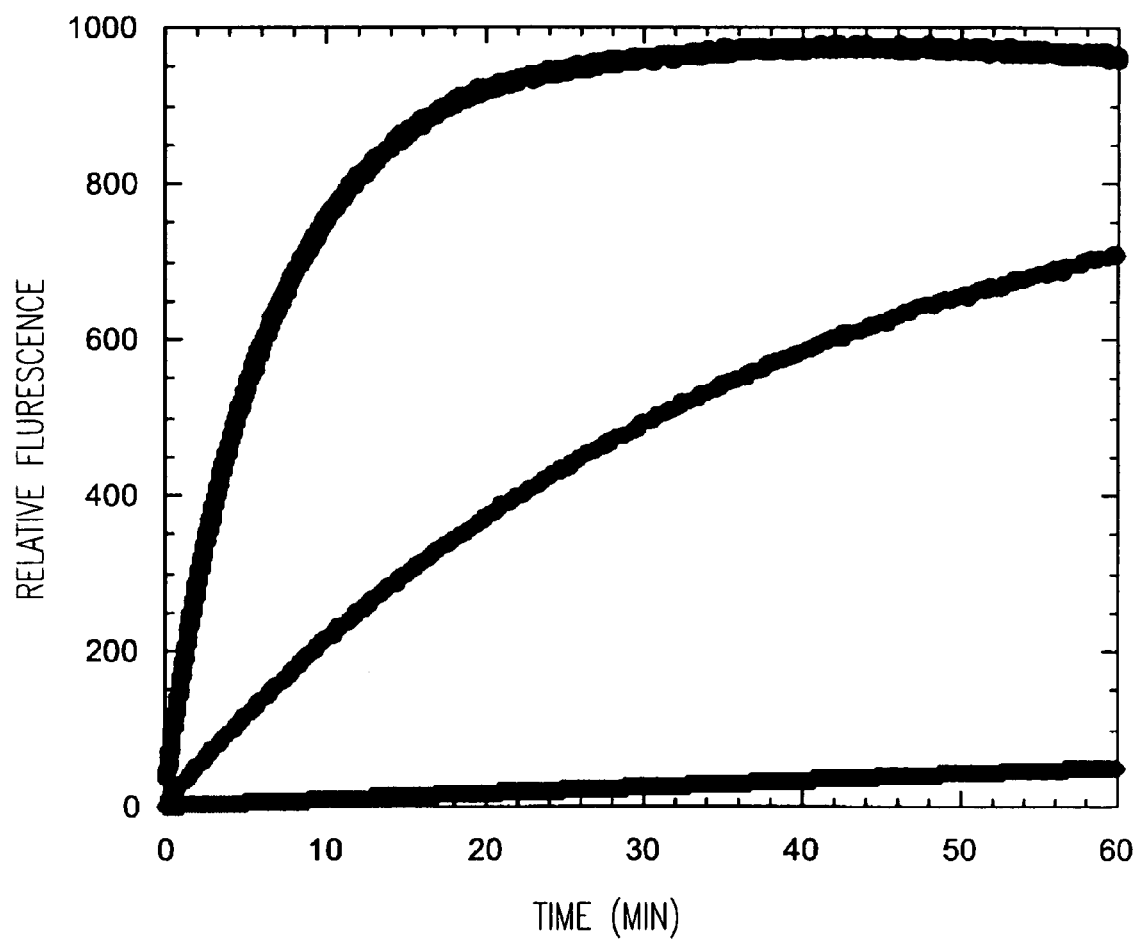
FIG. 4 illustrates the fluorophore release kinetics of PM2 in the presence of 0 mM (bottom curve), 0.01 mM (middle curve) or 0.05 mM DTT (top curve). The time sampling interval during the reaction was every 10 seconds.

The rate of Pacific Blue release was monitored in a continuous kinetic assay by modulating the reduction potential of the environment. As shown in FIG. 4, the rate of release of Pacific Blue from the interior of proteinoid microsphere preparation PM2 increased when the concentration of DTT was increased in the bulk buffer. The time sampling interval during the reaction was every 10 seconds. In the presence of 0 mM DTT, no appreciable increase in fluorescence emission intensity due to Pacific Blue release is observed (FIG. 4, bottom curve). Therefore, PM2 is stable in the absence of a reducing agent. However, when 0.01 mM DTT was added (FIG. 4, middle curve), the fluorescence emission intensity at 450 nm increases to steady state levels. When 0.01 mM DTT was added (FIG. 4, middle curve), the fluorescence emission intensity at 450 nm was linear over the course of the assay. A steeper and faster rate of release was observed when 0.05 mM DTT was added (FIG. 4, top curve).

Figure 5:
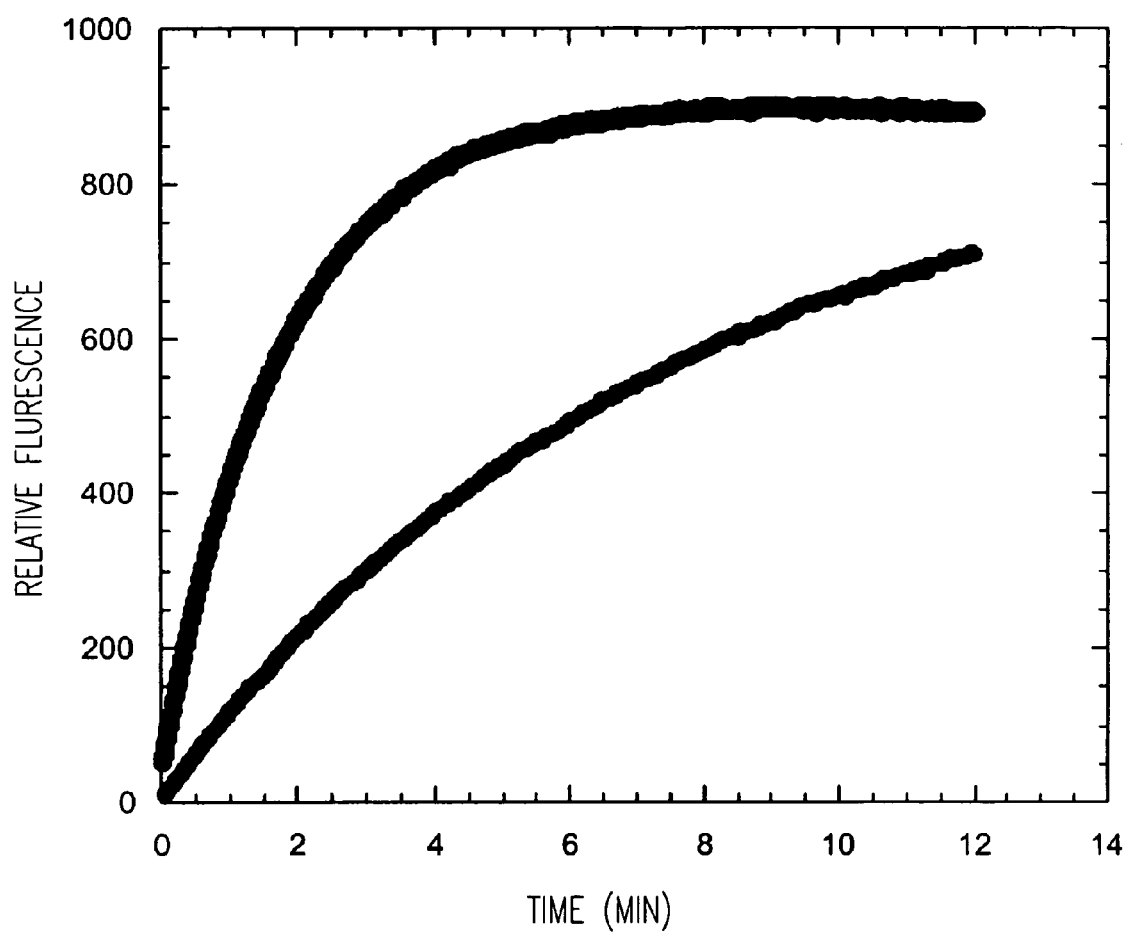
FIG. 5 illustrates the fluorophore release kinetics of PM1 in the presence of 0.01 mM, or 0.05 mM DTT (curves from bottom to top respectively). The time sampling interval during the reaction was every 1.0 seconds

The release rate of fluorophore from the proteinoid microsphere interior is dependent on the length of the cross-linking agent. As shown in FIG. 5, faster release kinetics are observed for PM1, which contains a C6 sized "window," than for PM2, which contains a C3 sized "window." FIG. 5 illustrates the fluorophore release kinetics of PM1 in the presence of 0.01 mM (bottom curve), or 0.05 mM DTT (top curve). The time sampling interval during the reaction was every 1.0 seconds. As noted in Example 1, the compositions of PM1 and PM2 differ only in the size of the alkane spacer of the cross-linker, and in the substitution of histidine for alanine. Accordingly, use of cross-linking agents with longer alkyl chains provides proteinoid microspheres with faster release rates.

Figure 6:
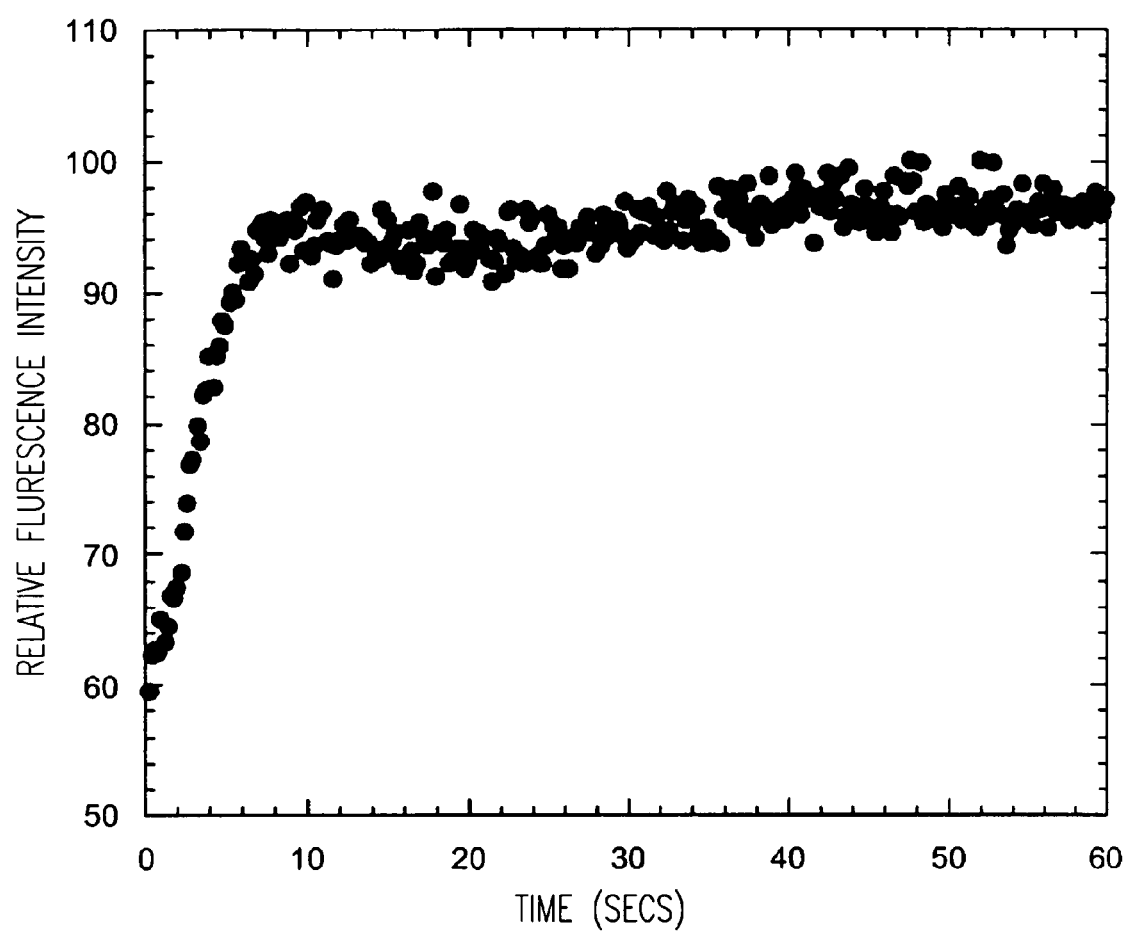
FIG. 6 illustrates the fluorophore release kinetics of PM3 in the presence of 1.0 mM, DTT. The time sampling interval during the reaction was every 100 ms.

FIG. 6 illustrates the fluorophore release kinetics of PM3 in the presence of 1.0 mM, DTT. The time sampling interval during the reaction was every 100 ms. As illustrated by FIG. 6, the fluorophore can be fully released from PM3 in approximately 10 seconds, compared to minute time scales with other DTT concentrations shown in FIGS. 7 and 8. However, larger amounts of the reducing agent must be used. Thus, it is possible to control the release time scale by varying the concentration of reducing agent.

Figure 7:
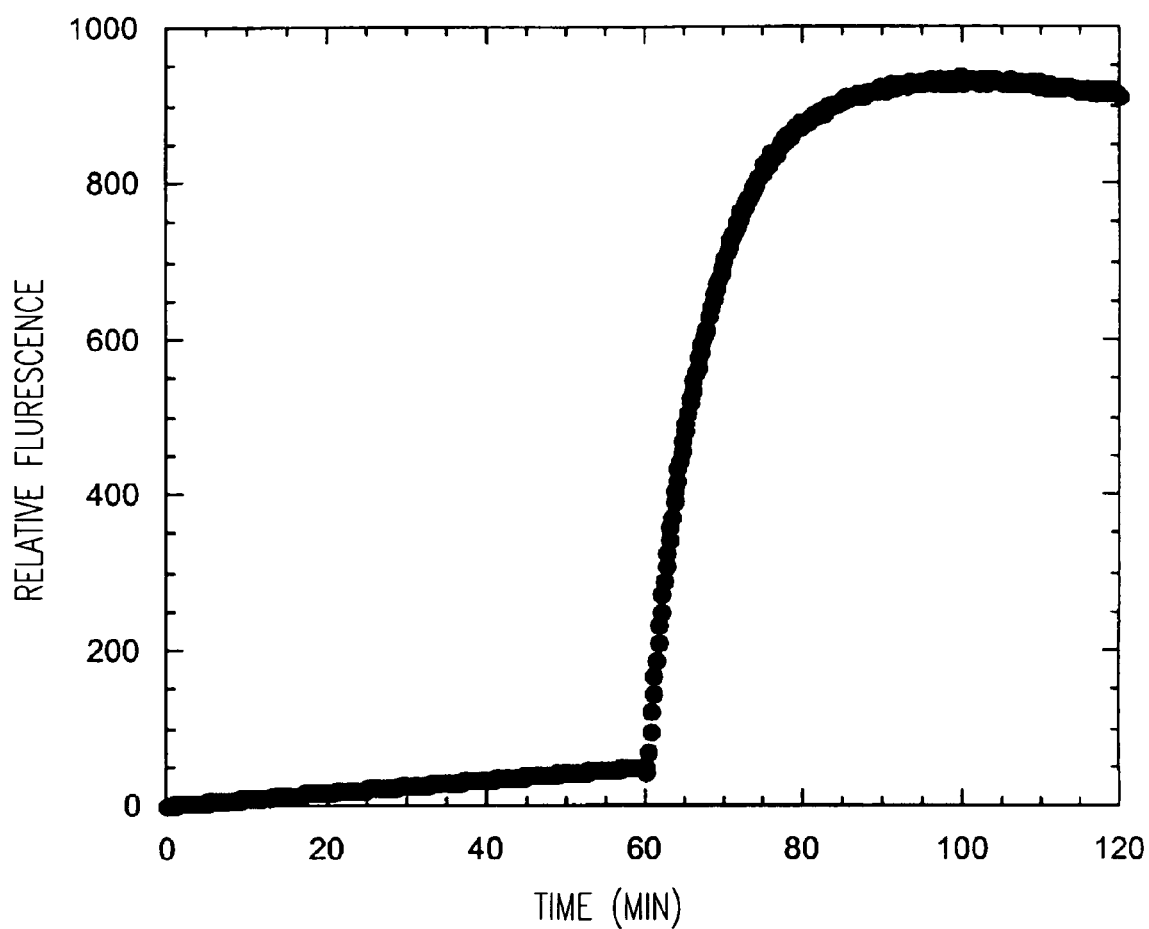
FIG. 7 illustrates the release of fluorophore from the PM1 preparation of proteinoid microspheres. PM1, at a concentration of 10% (v/v), was placed into a fluorometer cuvette at time zero and stirred for 60 minutes at 25° C. At 60 minutes, DTT is injected into the cuvette to a final concentration of 0.05 mM. Sampling time interval for the experiment was 15 seconds. These data illustrate that PM1 is stable until reduced by DTT.

FIG. 7 shows that loaded PM1 can be stirred in the fluorometer cuvette for an hour without appreciable increase in the emission fluorescence intensity at 450 nm. If DTT is injected into this cuvette to a final concentration of 0.05 mM, however, an instant increase in signal is observed. In this experiment, PM1 at a concentration of 10% (v/v) was placed into a fluorometer cuvette at time zero and stirred for 60 minutes at 25° C. At 60 minutes, DTT was injected into the cuvette to a final concentration of 0.05 mM. Sampling time interval for the experiment was 15 seconds. These results indicate that PM1 is stable until reduced. However, the fluorophore is released from the interior of PM1 when proteinoid microsphere is reduced by DTT.

The rate of release from proteinoid microspheres is primarily governed by the number of windows in the proteinoid microspheres that are opened to the interior during reduction. For a given proteinoid microsphere, which generally has uniform window size, it is possible to significantly alter the initial release rate simply by varying the amount of the cross-linker in the initial proteinoid mix. A fixed DTT concentration can be used for release.

Figure 8:
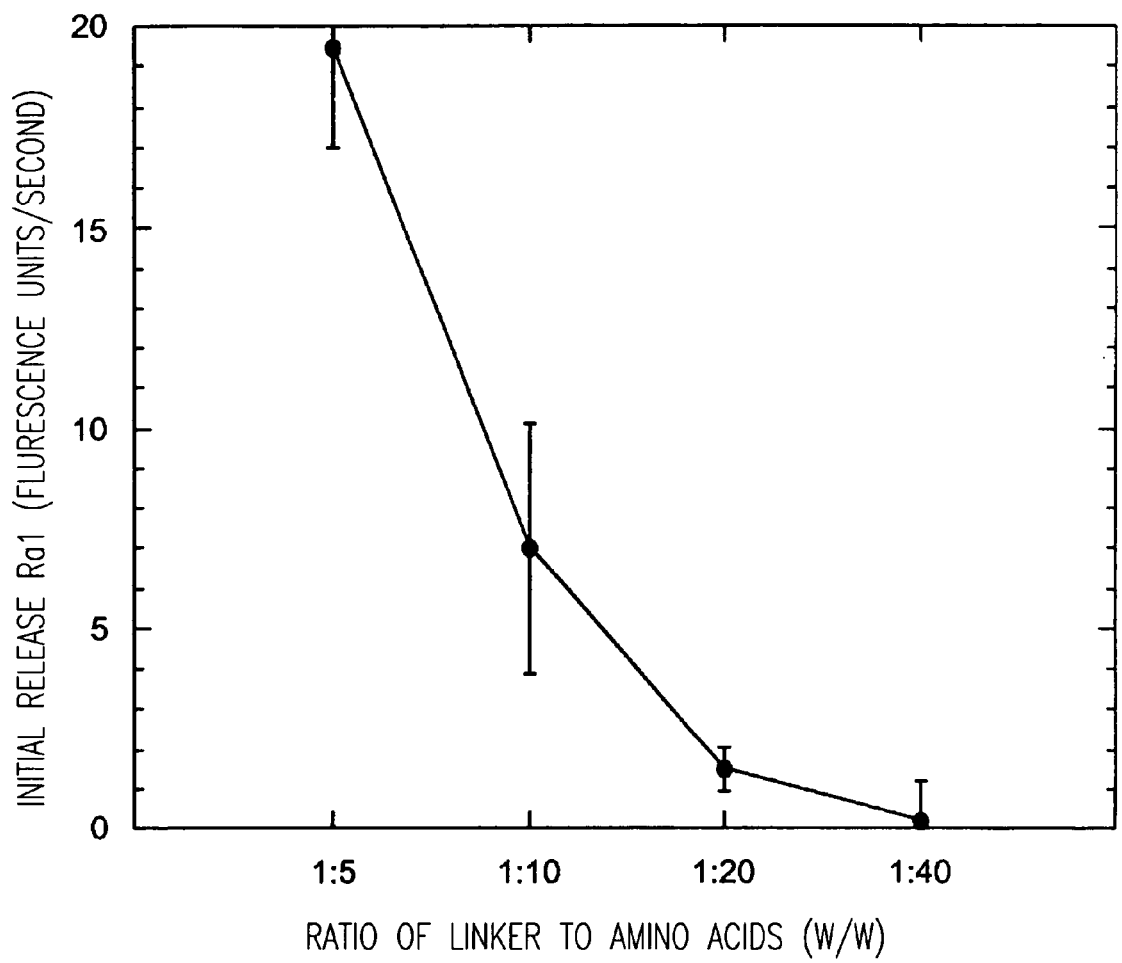
FIG. 8 provides a titration of the C6 homobifunctional cross-linker in PM1. Four PM1 constructs were prepared with various amounts of the cross-linker. Release of fluorophore from the proteinoid microsphere interior was monitored in the standard assay in the presence of 0.01 mM DTT. Plotted in the figure is the initial rate of release plotted as a function of the cross-linker: amino acid ratio. As can be seen in the figure, release rates can be slowed by having a minimal amount of cross-linker present when the proteinoid microsphere is formed. Also plotted is the standard deviation for each point determined from triplicate release runs.

FIG. 8 shows the result of measuring the initial release rate (in arbitrary fluorescence units per second) as a function of the amount of C6 cross-linking agent in PM1. Four PM1 constructs were prepared with various amounts of the cross-linker. Release of fluorophore from the proteinoid microsphere interior was monitored in the standard assay in the presence of 0.01 mM DTT. The initial rate of release is plotted in FIG. 8 as a function of the ratio of cross-linker to amino acid. As can be seen in FIG. 8, the more C6 reagent added to the amino acid mix at the time the proteinoid is formed, the faster the initial release rate. This arises from more reagent being incorporated into the proteinoid, and hence an increased number of windows opening up. Conversely, release rates can be slowed by using a minimal amount of cross-linker to form the proteinoid microsphere. It is therefore possible to fine tune release rates (from minutes to days time scales) for an environment of fixed reduction potential by controlling the amount of cross-linking reagent in the proteinoid mix.

EXAMPLE 3

Release from Proteinoid Microspheres in Serum

Figure 9:
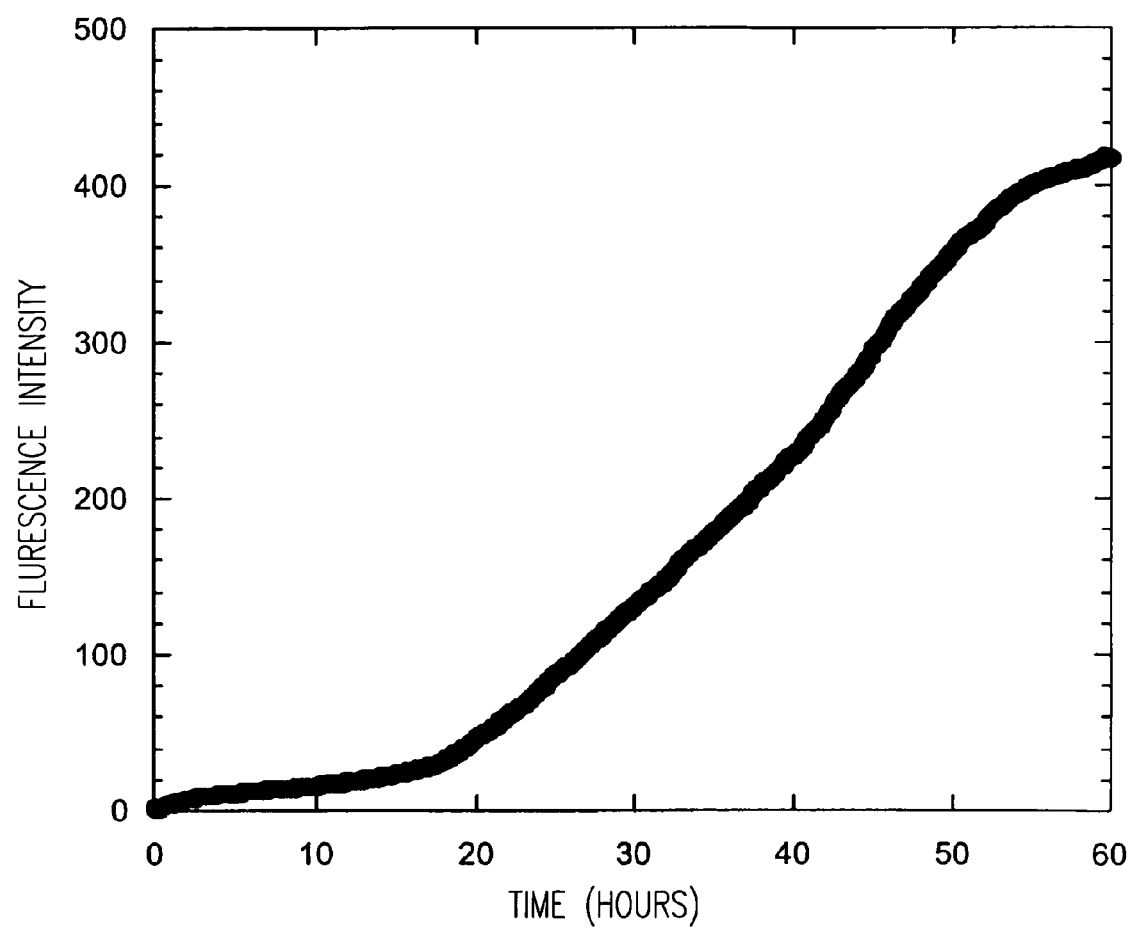
FIG. 9 graphically illustrates the release of fluorophore from PM1 proteinoid microspheres in human serum as a function of time. As illustrated, release is quite slow for the first approximate 18 hours, but the rate of release then increases to a steady almost linear rate of release that begins to plateau at approximately 55 hours.

The PM1 proteinoid microsphere preparation, loaded with Pacific Blue, was mixed with human serum to a final concentration of 10% (v/v). No reducing agent was added. The mixture was placed into a fluorometer cuvette and was slowly stirred for 60 hours. Fluorescence emission intensity at 450 nm (excitation wavelength 405 nm) was recorded as a function of time. The results are shown in FIG. 9. There was a small initial increase in fluorescence during the first two hours of the assay. During the next 18 hours, there was a slight linear increase in the amount of fluorophore released from the PM interior. At approximately 20 hours post mixing, there was an increase in the rate of Pacific Blue release, followed by a near plateau at 55 hours post mixing.

The release of Pacific Blue fluorophore spans a time course of nearly three days. These data indicate that serum has a low reduction potential comparable to buffer containing about 0.01 mM DTT. Although release rates were low, they were sustained, and such low, sustained release in actuality may be preferred for the delivery of a therapeutic agent into the blood. Proteinoid microspheres may also be used for treatment of open wounds, for example, chronic wounds, because human serum is a good simulant for wound exudate.

REFERENCES

Berger, G., 1984, [Hypotheses on the establishment of a genetic code and transfer of information from proteinoids to nucleic acids], *C R Acad Sci III* 299(9):333–8.

Brooke, S., and Fox, S. W., 1977, Compartmentalization in proteinoid microspheres, *Biosystems* 9(1):1–22.

Fox, S. W., and Harada, K., 1960, The thermal copolymerization of amino acids common to protein, *J. Am. Chem. Soc.* 82: 3745–51.

Fox, S. W., and Nakashima, T., 1974, Fractionation and characterization of an amidated thermal 1:1:1 proteinoid, *Biochemica et Biophysica Acta* 140: 155–167.

Fox, S. W., and Nakashima, T., 1980, The assembly and properties of protobiological structures: The beginnings of cellular peptide synthesis, *Biosystems* 12: 155–66.

Fox, S. W., Jungck, J. R., and Nakashima, T., 1974, From proteinoid microsphere to contemporary cell: formation of internucleotide and peptide bonds by proteinoid particles, *Orig Life* 5(1):227–37.

Fox, S. W., 1964, Thermal polymerization of amino acids and production of formed microparticles on lava, *Nature* 201: 336–37.

Fox, S. W., 1976, The evolutionary significance of phase-separated microsystems, *Orig Life* 7(1):49–68.

Fox, S. W., 1984, Self-sequencing of amino acids and origins of polyfunctional protocells, *Orig Life* 14(1–4): 485–8.

Fox, S. W., 1991, Synthesis of life in the lab? Defining a protoliving system, *Q Rev Biol* 66(2):181–5.

Green, N. S., Reisler, E., and Houk, K. N., 2001, Quantitative evaluation of the lengths of homobifunctional protein cross-inking reagents used as molecular probes, *Prot. Sci.*, 10:1293–1304.

Harada, K., and Fox, S. W., 1958, The thermal condensation of glutamic acid and glycine to linear peptides, *J. Am. Chem. Soc.* 80:2694–97.

Harada, K., and Fox, S. W., 1960, The thermal copolymerization of aspartic acid and glutamic acid, *Arch. of Biochem. Biophys.* 86:274–80.

Hartmann, J., Brand, M. C., and Dose, K., 1981, Formation of specific amino acid sequences during thermal polymerization of amino acids, *Biosystems* 13:141–47.

Hsu, L. L., Brooke, S., and Fox, S. W., 1971, Conjugation of proteinoid microspheres: a model of primordial communication, *Curr Mod Biol* 4(1):12–25.

Hsu, L. L., and Fox, S. W., 1976, Interactions between diverse proteinoids and microspheres in simulation of primordial evolution, *Biosystems* 8(2):89–101.

Ishima, Y., Przybylski, A. T., and Fox, S. W., 1981, Electrical membrane phenomena in spherules from proteinoid and lecithin, *Biosystems* 13(4):243–51.

Jungck, J. R., and Fox, S. W., 1973, Synthesis of oligonucleotides by proteinoid microspheres acting on ATP, *Naturwissenschaften* 60(9):425–7.

Kokufuta, E., Sakai, H., and Harada, K., 1983, Factors controlling the size of proteinoid microspheres, *Biosystems* 16(3–4):175–81.

Lakowicz, J. R. (1983). *Principles of Fluorescence Spectroscopy*, Chapter 10, Plenum Press, New York, London.

Luque-Romero, M. M., de Medina, L. S., and Blanco, J. M., 1986, Fractionation and amino acid composition of an aspartic acid-containing thermal proteinoid population, *Biosystems* 19(4):267–72.

Ma, X., Santiago, N., Chen, Y. S., Chaudhary, K., Milstein, S. J., and Baughman, R. A., 1994, Stability study of drug-loaded proteinoid microsphere formulations during freeze-drying, *J Drug Target* 2(1):9–21.

Madhan Kumar, A. B., and Panduranga Rao, K., 1998, Preparation and characterization of pH-sensitive proteinoid microspheres for the oral delivery of methotrexate, *Biomaterials* 19(7–9):725–32.

Masinovsky, Z., Lozovaya, G. I., Sivash, A. A., and Drasner, M., 1989, Porphyrin-proteinoid complexes as models of prebiotic photosensitizers, *Biosystems* 22(4):305–10.

Masinovsky, Z., 1995, [The origin and early development of biological catalysts], *Cas Lek Cesk* 134(19):607–10.

Matsuno, K., 1981, Self-sustaining multiplication and reproduction of microsystems in protobiogenesis, *Biosystems* 14(2):163–70.

Matsuno, K., 1981b, Material self-assembly as a physiochemical process, *Biosystems* 13:237–241.

Matsuno, K., 1984, Electrical excitability of proteinoid microspheres composed of basic and acidic proteinoids, *Biosystems* 17(1):11–4.

McAlhaney, W. W., and Rohlfing, D. L., 1976, Formation of proteinoid microspheres under simulated prebiotic atmospheres and individual gases, *Biosystems* 8(2):45–50.

Muller-Herold, U., and Nickel, G., 1994, The stability of proteinoid microspheres, *Biosystems* 33(3):215–20.

Nakashima, T., and Fox, S. W., 1980, Synthesis of peptides from amino acids and ATP with lysine-rich proteinoid, *J Mol Evol* 15(2):161–8.

Nakashima, T., and Fox, S. W., 1981, Formation of peptides from amino acids by single or multiple additions of ATP to suspensions of nucleoproteinoid microparticles, *Biosystems* 14(2):151–61.

Phillips, R. D., and Melius, P., 1974, The thermal polymerization of amino acids, *Int. J Peptide Protein Res.* 6:309–319.

Przybylski, A. T., Stratten, W. P., Syren, R. M., and Fox, S. W., 1982, Membrane, action, and oscillatory potentials in simulated protocells, *Naturwissenschaften* 69(12):561–3.

Przybylski, A. T., 1985, Excitable cell made of thermal proteinoids, *Biosystems* 17(4):281–8.

Rohlfing, D. L., 1975, Coacervate-like microspheres from lysine-rich proteinoid, *Orig Life* 6(1–2):203–9.

Ryan, J. W., and Fox, S. W., 1973, Activation of glycine by ATP, a divalent cation, and proteinoid microspheres, *Curr Mod Biol* 5(3):115–8.

Santiago, N., Milstein, S., Rivera, T., Garcia, E., Zaidi, T., Hong, H., and Bucher, D., 1993, Oral immunization of rats with proteinoid microspheres encapsulating influenza virus antigens, *Pharm Res* 10(8):1243–7.

Snyder, W. D., and Fox, S. W., 1975, A model for the origin of stable protocells in a primitive alkaline ocean, *Biosystems* 7(2):222–9.

Syren, R. M., Sanjur, A., and Fox, S. W., 1985, Proteinoid microspheres more stable in hot than in cold water, *Biosystems* 17(4):275–80.

The references and disclosures cited herein incorporated by reference in their entirety.

What is claimed is:

1. A method of releasing a therapeutic agent from a proteinoid microsphere comprising introducing a therapeutic agent encapsulated with a proteinoid microsphere comprising a mixture of amino acids that are thermally condensed and crosslinked with a crosslinker of any one of the formulae I-VI into a reducing environment:

$$COOH-S-S-(CH_2)_n-S-S-COOH \qquad I$$

$$COOH-S-S-X-S-S-COOH \qquad II$$

NH2—S—S—(CH2)$_n$—S—S—NH2  III

NH2—S—S—X—S—S—NH2  IV

Aryl—S—S—(CH2)$_n$—S—S—Aryl  V

Aryl—S—S—X—S—S—Aryl  VI wherein:
- X is a spacer group of about 3 to 100 angstroms by about 2 to 30 angstroms that comprises an alkane chain, an alkene chain, a cycloalkyl or aryl ring having five to fourteen carbon atoms, or a combination thereof;
- n is an integer ranging from 1 to 18;
- S is a sulfur atom; and
- Aryl is a phenyl radical or an ortho-fused bicyclic radical having about nine to ten ring atoms wherein at least one ring is aromatic and wherein each Aryl moiety is substituted with at least one reactive group that can form a covalent linkage with an amino acid.

2. The method of claim 1 wherein the reactive group that can form a covalent linkage with an amino acid is carboxylate, nitro, amino or sulfhydryl.

3. The method of claim 1 wherein the reactive group that can form a covalent linkage with an amino acid is a carboxylate group.

4. The method of claim 1 wherein the therapeutic agent is released from the proteinoid microsphere into a wound.

5. The method of claim 4 wherein the wound is a chronic wound.

6. The method of claim 1 wherein the therapeutic agent is released from the proteinoid microsphere into the bloodstream of a mammal.

7. The method of claim 1 wherein the therapeutic agent is released from the proteinoid microsphere into the digestive track of a mammal.

8. The method of claim 1 wherein the reducing environment is serum.

9. A method of releasing a therapeutic agent from a proteinoid microsphere comprising introducing a therapeutic agent encapsulated with a proteinoid microsphere comprising a mixture of amino acids that are thermally condensed and crosslinked with a crosslinker reagent of formula VII into a reducing environment:

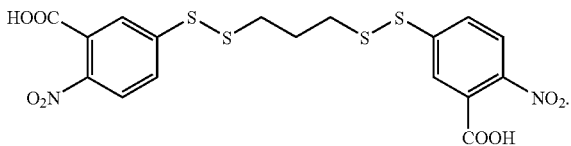

10. The method of claim 9 wherein the therapeutic agent is released from the proteinoid microsphere into a wound.

11. The method of claim 10 wherein the wound is a chronic wound.

12. A method of sustained release of a therapeutic agent into the bloodstream of a mammal comprising administering a therapeutic agent encapsulated within a proteinoid microsphere to the bloodstream of a mammal mammal, wherein the proteinoid microsphere comprises a mixture of amino acids that are thermally condensed and crosslinked with a crosslinker of any one of the formulae I–VI:

COOH—S—S—(CH2)$_n$—S—S—COOH  I

COOH—S—S—X—S—S—COOH  II

NH2—S—S—(CH2)$_n$—S—S—NH2  III

NH2—S—S—X—S—S—NH2  IV

Aryl—S—S—(CH2)$_n$—S—S—Aryl  V

Aryl—S—S—X—S—S—Aryl  VI wherein:
- X is a spacer group of about 3 to 100 angstroms by about 2 to 30 angstroms that comprises an alkane chain, an alkene chain, a cycloalkyl or aryl ring having five to fourteen carbon atoms, or a combination thereof;
- n is an integer ranging from 1 to 18;
- S is a sulfur atom; and
- Aryl is a phenyl radical or an ortho-fused bicyclic radical having about nine to ten ring atoms wherein at least one ring is aromatic and wherein each Aryl moiety is substituted with at least one reactive group that can form a covalent linkage with an amino acid.

13. The method of claim 12 wherein the reactive group that can form a covalent linkage with an amino acid is carboxylate, nitro, amino or sulfhydryl.

14. The method of claim 12 wherein the reactive group that can form a covalent linkage with an amino acid is a carboxylate group.

15. A method of sustained release of a therapeutic agent into the bloodstream of a mammal comprising administering a therapeutic agent encapsulated with a proteinoid microsphere to the bloodstream of a mammal, wherein the proteinoid microsphere comprises a mixture of amino acids that are thermally condensed and crosslinked with a crosslinker reagent of formula VII:

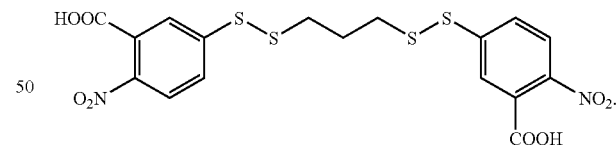

* * * * *